US009196840B2

(12) United States Patent
Cote et al.

(10) Patent No.: US 9,196,840 B2
(45) Date of Patent: *Nov. 24, 2015

(54) FLUOROACYLATED ARYLAMINES

(71) Applicant: Xerox Corporation, Norwalk, CT (US)

(72) Inventors: Adrien P Cote, Clarkson (CA); Richard A Klenkler, Oakville (CA); Amanda L Bongers, Ottawa (CA); Gregory M McGuire, Oakville (CA)

(73) Assignee: Xerox Corporation, Norwalk, CT (US)

( * ) Notice: Subject to any disclaimer, the term of this patent is extended or adjusted under 35 U.S.C. 154(b) by 153 days.

This patent is subject to a terminal disclaimer.

(21) Appl. No.: 13/682,764

(22) Filed: Nov. 21, 2012

(65) Prior Publication Data

US 2014/0142340 A1    May 22, 2014

(51) Int. Cl.
*C07C 211/00* (2006.01)
*H01L 51/00* (2006.01)
*G03G 5/06* (2006.01)
*H01L 51/50* (2006.01)

(52) U.S. Cl.
CPC .......... *H01L 51/0059* (2013.01); *G03G 5/0603* (2013.01); *G03G 5/0614* (2013.01); *H01L 51/5048* (2013.01)

(58) Field of Classification Search
CPC .................................................... H01L 51/0059
See application file for complete search history.

(56) References Cited

U.S. PATENT DOCUMENTS

| 5,202,408 | A   |   | 4/1993  | Yanus et al.         |
|-----------|-----|---|---------|----------------------|
| 7,652,148 | B1  |   | 1/2010  | Cote et al.          |
| 8,754,260 | B2  | * | 6/2014  | Cote et al. ........ 564/314 |
| 8,883,383 | B2  | * | 11/2014 | Cote et al. ...... 430/58.65 |
| 9,070,886 | B2  | * | 6/2015  | Cote et al. ........ 564/307 |

* cited by examiner

*Primary Examiner* — Clinton Brooks
(74) *Attorney, Agent, or Firm* — MDIP LLC

(57) ABSTRACT

Novel fluoroacyl arylamines useful in organic electronic applications are disclosed, including methods of synthesizing those fluoroacyl arylamines using Lewis acids for acyl moiety activation.

11 Claims, No Drawings

FLUOROACYLATED ARYLAMINES

FIELD

Novel fluoroacylated arylamine compounds are provided. The compounds have favorable electroactivity and are suitable for organic electronic applications.

BACKGROUND

Arylamines are used in electronics applications including use in photoreceptors, thin film transistors (TFT), photovoltaic (PV) cells, light emitting diodes (LEDs) etc. In the electrophotographic imaging field, the photoactive portions of components can be composed of organic materials such as the fluoroacylated arylamines of interest which act as photoreceptors for temporarily forming an image in the form of a pattern of charges on the photoreceptor.

Arylamines and arylamine derivatives are known but none comprise a fluoroacyl moiety or the altered electronic properties of the compounds described herein. The synthesis of the compounds of interest as provided herein avoids a Friedel-Crafts acylation reaction using a Lewis acid, such as, aluminum trichloride, to activate the acyl entities for addition to arylamine phenyl rings.

SUMMARY

Disclosed herein are certain fluoroacyl arylamines with beneficial electro activity. A fluoroacyl arylamine can be a symmetric molecule.

In embodiments, fluoroacyl arylamines are prepared without Lewis acids and a Friedel-Crafts acylation reaction as is normally practiced in the art. Fluoroacyl arylamines are obtained from an arylamine and a trifluoroacyl-donating reagent, such as, trifluoroacetic anyhydride, compounds containing a trifluoroacetic anhydride group and so on, in a single reaction scheme without using a Lewis acid.

Those and other features and advantages of various embodiments of materials, devices, systems and/or methods relating to making and using certain fluoroacylated arylamines of interest are described in or are apparent from the following description.

DESCRIPTION

While not wishing to be bound by any particular theory, the one or more fluoroacyl groups added to an arylamine as produced by the present method of interest, impart new electronic properties and configurations to conventional arylamine electronic material. Hence, the arylamines carrying one or more fluoroacyl groups have different and/or improved properties, such as, charge transport properties, and are useful for a number of different electronic and other industrial uses.

For example, a fluoroacyl arylamine of interest can be used as a charge transport molecule in a photoreceptor. The one or more fluoroacyl moieties alter the charge distribution of the parent arylamine bestowing a fluoroacyl arylamine with different electronic, such as, charge transport, properties from the base arylamine.

The fluoroacyl arylamine may be formed into a thin coating alone or by using a suitable film-forming material to result, for example, in a charge transport layer (CTL). The film-forming material can be a transparent organic polymer or non-polymeric material capable of supporting the injection of photogenerated holes or electrons and capable of allowing the transport of the holes/electrons through the CTL to selectively discharge the charge on the surface of the imaging device component, such as, a photoreceptor. The CTL containing the fluoroacyl arylamine exhibits substantial optical transparency with insignificant light absorption and negligible charge generation when exposed to a wavelength of light useful in, for example, photocopying devices, e.g., from about 400 nm to about 900 nm.

Hence, a CTL can comprise a film-forming material; a fluoroacyl arylamine of interest; and an optional lubricant. The lubricant, such as, a fluorinated resin, such as a polytetrafluoroethylene (PTFE) and the like, can be present in an amount, relative to the total, of from about 1% to about 15%; from about 3% to about 10%; from about 8% to about 9% by weight of the layer. The fluoroacylated arylamine can be present in an amount, relative to the total, from about 20% to about 50% of the CTL; from about 25% to about 45%; from about 30% to about 40% by weight. The remainder can comprise the film-forming material and any optional additives, as a design choice. (The above amounts and percentages, including those presented elsewhere in the specification, are in terms of and relative to w/v, w/w or v/w as appropriate for the material(s).)

Any suitable and conventional technique may be used to mix and thereafter to apply the CTL coating mixture to a photoreceptor under construction. Typical application techniques include spraying, dip coating, roll coating, wire wound rod coating and the like. Drying of the deposited coating may be obtained by any suitable conventional technique, such as, oven drying, infrared drying, air drying and the like.

The CTL can be an insulator to the extent that the electrostatic charge placed on the CTL is not conducted in the absence of illumination at a rate sufficient to prevent formation and retention of an electrostatic latent image thereon. In general, the ratio of the thickness of the CTL to the charge generating layer can be from about 2:1 to about 200:1, in instances, as great as about 400:1.

The thickness of the CTL can be from about 5 µm to about 200 µm, from about 15 µm to about 40 µm. The CTL may comprise dual layers or plural layers, and each layer may contain different concentrations of a charge transporting component or may contain different charge transporting components.

The CTL also can serve other functions, such as, serving as a protective coating.

The term, "arylamine," refers, for example, to moieties containing both aryl and amine groups. Arylamines can have the structure Ar—NRR', in which Ar represents an aryl group and R and R' are groups that independently may be selected from hydrogen and substituted or unsubstituted alkyl, alkenyl, aryl and other suitable hydrocarbons and/or functional groups. The term, "triarylamine," refers, for example, to arylamine compounds having the general structure NArAr'Ar", in which Ar, Ar' and A" represent independently selected aryl groups, which may be substituted, functionalized and so on.

A fluoroacyl arylamine may be a symmetric molecule. In certain embodiments of the present invention, the fluoroacyl arylamine of interest may be a planar molecule, particularly when held by hydrogen bonds from the fluoroacyl moiety to the core arylamine structure.

In an embodiment, an arylamine substrate of interest comprises the structure:

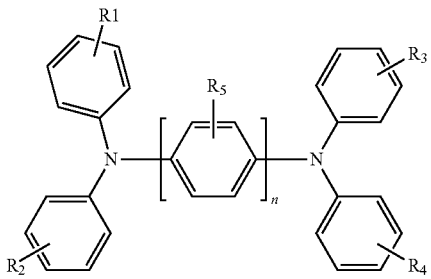

where $R_1$, $R_2$, $R_3$, $R_4$ and $R_5$ may be located at any site on a phenyl group; and can be one or more hydrogen atoms; a halogen; a hydrocarbon, which can be saturated, substituted or contain a heteroatom, such as, N, O, S and so on, of 1 to about 8 carbon atoms, for example, alkyl, alkenyl, aryl, hydroxyl, oxyalkyl and so on; or a functional group comprising a reactive moiety or site; and n is 0, 1, 2 or 3. A functional group can comprise a hydroxyl group, a carbonyl group, a halogen, an amino group and so on as a design choice.

A trifluoroacyl-donating reagent can be an acid, an anhydride thereof and so on. An example of an anhydride is one with the formula:

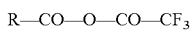

where R may be $CF_3$, alkyl, aryl, substituted alkyl or substituted aryl, where the substitutions may be halogen, hydroxy or nitro, and wherein the alkyl or aryl may have between 1 and about 8 carbon atoms.

The synthesis reaction occurs in a suitable solution or solvent which dissolves both the trifluoroacyl-donating reagent, such as, a trifluoro anhydride, such as, trifluoroacetic anhydride, and the arylamine reagent, and is inert to the reaction between the two substrates or reactants. The liquid reaction mixture may comprise one compound or a mixture of two or more compounds. In embodiments, the reaction solution is not miscible significantly with water so that the resulting product may be isolated by phase separation. Suitable liquids or solvents include hydrocarbons, ethers, long chain alcohols, hydrocarbons derivatized by halogens, ethers or long chain alcohols and mixtures thereof. Compatible liquids with higher boiling points may be used to allow the reaction to occur at a higher temperature. Examples include halogenated hydrocarbons, aliphatic nitriles, alkanes and so on, such as, but not limited to, dicholoromethane, hexane and acetonitrile.

In an embodiment, the arylamine may be structure A or B:

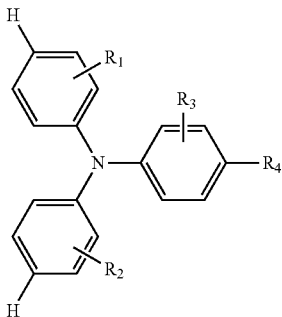

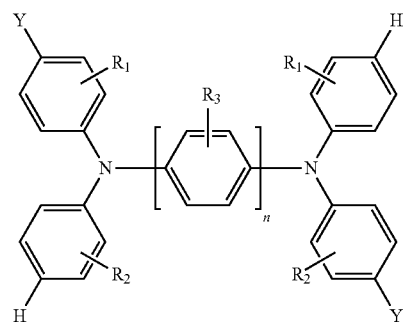

wherein Y is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; $R_1$ $R_2$ and $R_3$ each is hydrogen, $C_1$-$C_5$ alkyl, $C_3$-$C_7$ cyclic alkyl, $C_1$-$C_4$ alkoxy, hydroxy, ω-hydroxy substituted $C_2$-$C_8$ alkyl, halogen or aryl, optionally substituted with $C_1$-$C_5$ alkyl; $R_4$ is hydrogen, $C_1$-$C_5$ alkyl, $C_3$-$C_7$ cyclic alkyl, hydroxy, ω-hydroxy substituted $C_2$-$C_8$ alkyl, halogen or aryl optionally substituted with $C_1$-$C_5$ alkyl; and n is 0, 1, 2 or 3.

In another embodiment, structure A may be:

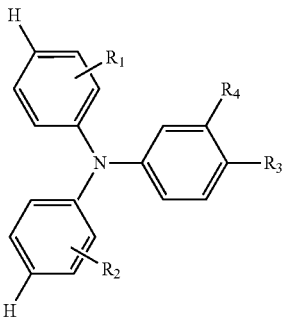

wherein $R_1$, $R_2$, $R_3$ and $R_4$ are as defined above.

In another embodiment, structure B has a structure:

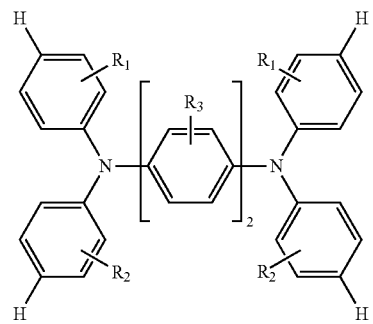

wherein $R_1$, $R_2$ and $R_3$ are as defined above.

Alternatively, compound B has a structure:
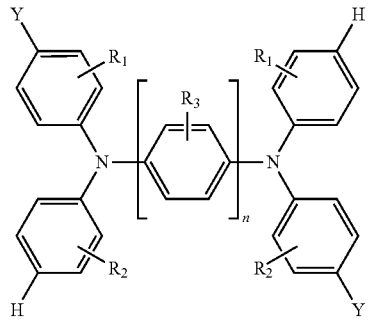
wherein Y is methyl, and n, $R_1$, $R_2$ and $R_3$ are as defined above.
In another embodiment, the arylamine is selected from the group consisting of:
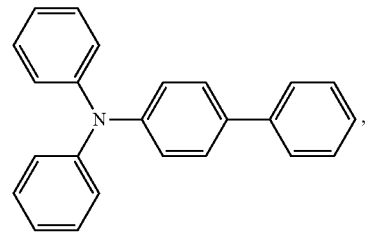
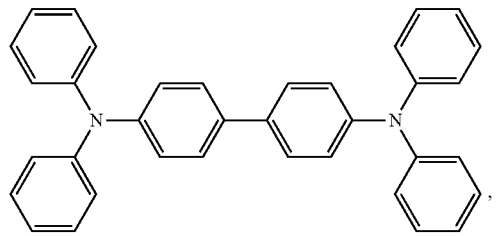
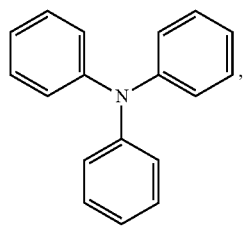
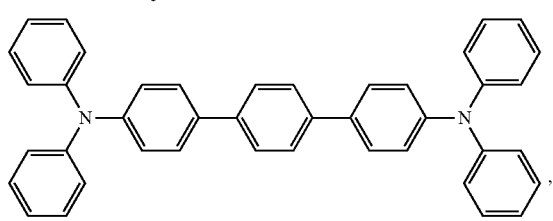
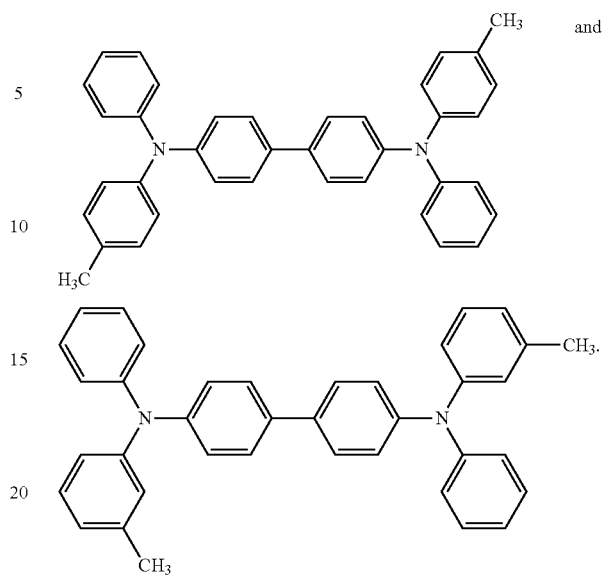
In embodiments, a fluoroacyl arylamine of interest comprises
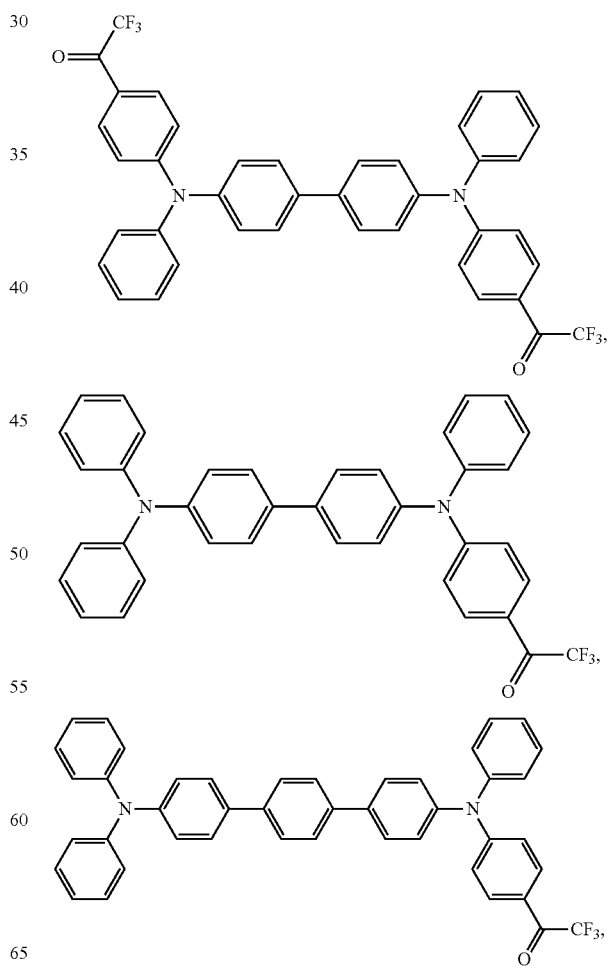

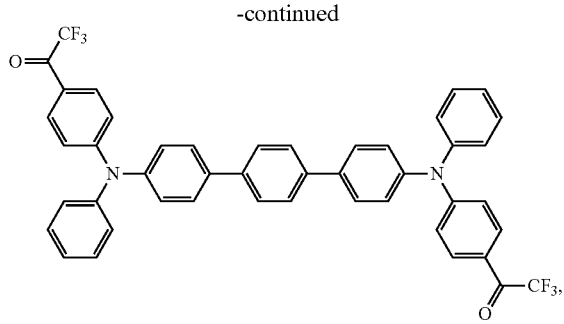

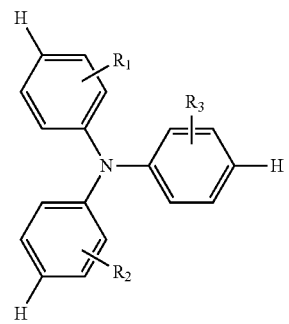

wherein $R_1$, $R_2$ and $R_3$ are as defined above; and at least one ring comprises at least one fluoroacyl moiety,

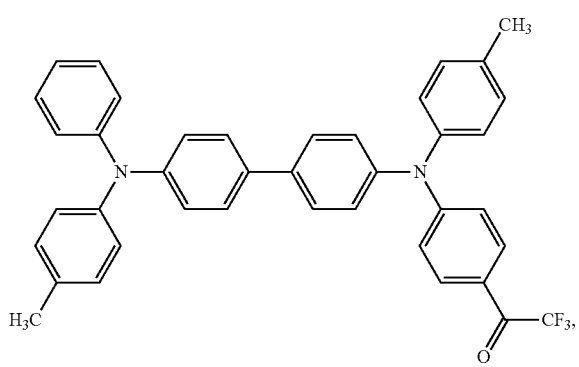

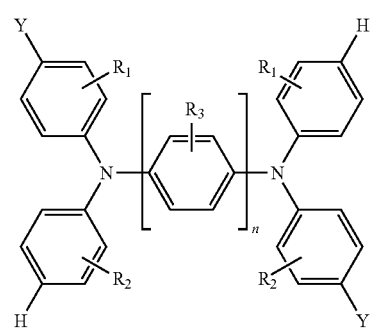

wherein n, Y, $R_1$, $R_2$ and $R_3$ are as defined above; and at least one ring comprises at least one fluoroacyl moiety,

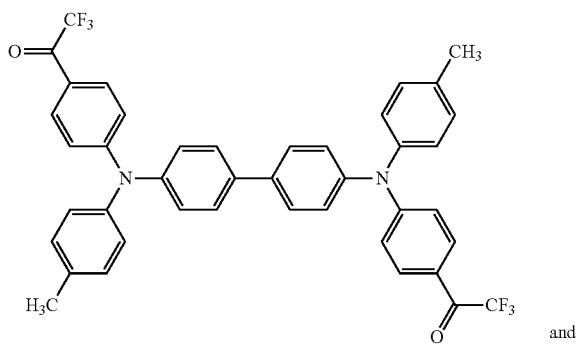

and

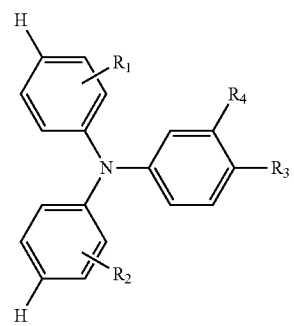

wherein $R_1$, $R_2$, $R_3$ and $R_4$ are as defined above, and one or more rings comprise at least one fluoroacyl moiety; or

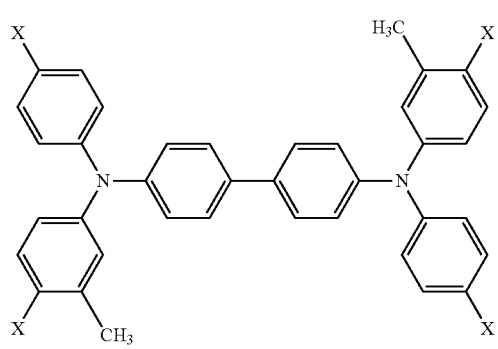

wherein, X is a fluoroacyl group or hydrogen and the number of fluoroacyl groups ranges from 1 to 4,

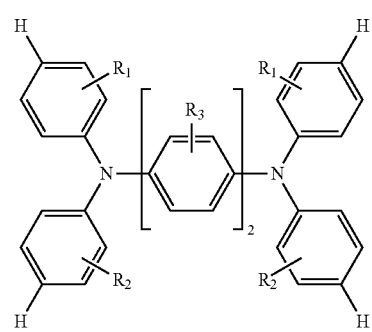

wherein $R_1$, $R_2$ and $R_3$ are as defined above, and one or more of the rings comprise at least one fluoroacyl moiety.

In embodiments, the temperature and pressure of the reaction are such that the reaction mixture remains in liquid form and continues to dissolve all of the chemical reactants and products. The conditions may vary with the reactants and/or liquid reagent(s) used.

The reaction may occur in a reactor maintained at room temperature or slightly higher. In embodiments, the reaction temperature can be from about 25° C. to about 90° C., from about 30° C. to about 80° C., from about 40° C. to about 70° C. Higher temperatures may be used with suitable reagents which do not become overly volatile at those elevated temperatures. Higher temperatures may be used to increase the rate of reaction. To reduce liquid loss or to facilitate reaction kinetics, the reaction may occur under reflux, occur in closed conditions or under pressure, for example.

The reaction time may vary with the temperature and individual starting materials. The more reactive the trifluoroacyl-donating compound and/or the higher the temperature, reaction time may be abbreviated. The reaction time also may vary with the particular arylamine substrate and the number and location of fluoroacyl moieties that are incorporated in the product.

During the reaction, progress may be monitored by observation of reaction color, reaction turbidity and so on, which parameters can be monitored visually or using an appropriate sensor. A sample may be removed periodically and analyzed, for example, by HPLC or other analytic method, or a sample may flow from the main reaction vessel by or through a sensor or other monitoring device, such as, a spectrophotometer.

After the reaction is completed, the final product resembles the arylamine substrate but with one or more fluoroacyl moieties attached to one or more of the pendant aryl moieties. In embodiments, the fluoroacyl moiety can be attached in the para position, however, the fluoroacyl residue can be located at other positions on an aryl ring. Also, any one aryl group may contain more than one fluoroacyl group. An acid byproduct also may be produced from an acid anhydride reagent.

The final fluoroacyl arylamine product can be separated by removal, precipitation and/or inactivation of any reagent or byproduct, such as, an acid byproduct when using an anhydride, such as, by neutralization. The solution also can be removed, such as, by evaporation and/or precipitating the product. Acid byproducts, such as, trifluoroacetic acid when an anhydride is used, can be dissolved in aqueous solutions and may be washed with aqueous or ionic liquids to be separated from the fluoroacyl arylamine-containing solution. The final fluoroacyl arylamine product also may be dried to remove residual liquid reactants and water, for example, by vacuum and/or heat. Complete removal of liquid reactants and reagents and/or water may be determined when the weight remains constant.

Because of the reaction scheme and kinetics, little may need to be done to purify the fluoroacyl arylamine compound from the reaction mixture, although additional separation, filtration and/or purification processes can be conducted, as desired, to a desired purity level or as needed, for example, based on the starting reagents. For example, the desired fluoroacylated arylamine product can be subjected to conventional organic washing steps, can be separated, can be decolorized (if necessary), treated with known absorbents (such as silica, alumina, carbon, clays and the like, if necessary) and the like. The final product can be isolated, for example, by a suitable precipitation or crystallization procedure. Such procedures are conventional and will be apparent to those skilled in the art.

The resulting fluoroacylated arylamine may have 1, 2 or more fluoroacyl moieties attached to any of the aromatic rings at any position. Certain positions of attachment may be selected as a design choice from a reaction standpoint, others may be synthesized by adjusting the reaction conditions and trifluoroacyl-donating molecule. The molar amount of trifluoroacyl-donating molecule in the reaction can determine the number of fluoroacyl moieties attached to the arylamine core structure.

The fluoroacylated arylamine can be used as a final product or can be further processed and/or reacted to provide other compounds for similar or different uses. For example, the fluoroacylarylamine may be used in a composition, for example, as a charge transport molecule in a CTL of an electrophotographic imaging member. The compounds of interest comprise one or more reactive carbonyl groups or can be synthesized to comprise other functional or reactive groups. Hence, the compounds of interest can be used as reagent for producing other compounds, polymers and so on, practicing materials and methods known in the art as a design choice. Hence, the fluoroacyl arylamine molecules can be used to produce polymers and copolymers resulting from chemical reaction(s) to add additional reactive moieties or functional groups to the fluoroacyl arylamine core where the functional groups can react in a polymerization reaction; polymerization of fluoroacyl arylamine molecules; further derivatization of fluoroacyl arylamines; using a fluoroacyl arylamine as a starting material to synthesize another novel compound retaining the basic fluoroacyl arylamine structure; and so on.

The reaction of interest produces product in high yield, high purity or both without byproduct (other than the intended acid byproduct when an anhydride is used) or starting material contamination. In bench top laboratory experiments, yields of about 70% or more are obtained with purities routinely greater than about 90%.

The synthesis reaction of interest does not require or use a Lewis acid or other metal, which later needs to be removed or which can interfere with purification of the fluoroacyl arylamine product.

Traditionally, multiple chemical reactions were required to synthesize different arylamines. On the other hand, the reaction of interest may be done simply, for example, in a single vessel, as a one-step reaction or both without need for multiple reactions, multiple reagent introductions, complicated purification schemes and so on, which incur cost and make product purity more difficult to obtain.

The final chemical structure of the fluoroacyl arylamine product may be determined by, for example, HPLC, LC/MS, $^1$H NMR, $^{19}$F NMR, FT-IR, elemental analysis, crystallography and so on.

As used herein, "light," refers to any electromagnetic radiation of any wavelength regardless of whether visible to the human eye. For example, ultraviolet light and infrared light are included. Also, "light," encompasses multiwavelengths as well as single wavelength light. The term, "light," also includes that with at least partial congruent wavelengths, such as a laser.

A number of different organic electronic devices may incorporate the fluoroacyl arylamine as a component. A fluoroacyl arylamine can be used in hole and/or electron transfer layers in devices which convert electrical energy into radiation, detect signals through electronic processes, convert radiation into electrical energy, or other uses where one or more organic semiconductor layers are desired. Organic electronic devices can include a conductive layer (such as an electroactive or photoactive layer) positioned between two electrodes. In some devices, a CTL can be utilized between the conductive layer and an electrode. For example, a hole transport layer can be positioned between the conductive layer and the anode and an electron transport layer can be positioned between the conductive layer and the cathode. Thus, the new materials may be used in organic electronic devices.

The term, "organic electronic device," is intended to mean a device comprising an organic compound-containing device or component including, for example, one or more semiconductor layers or materials. The device may have either active electronic components or passive electronic components. Organic electronic devices include, but are not limited to:

a. devices that convert electrical energy into radiation (such as, a light-emitting diode, light emitting diode display, light emitting electrochemical cell, electrogenerated chemiluminescence, diode laser, infra-red emitters electroluminescence or lighting panel);

b. devices that detect electrical or light signals through electronic processes such as photodetectors, photoconductive cells, photoresistors, photoswitches, phototransducers, phototransistors, phototubes, infrared detectors, or biosensors, photoconductive diodes, and other optical or electrical sensors;

c. devices that convert radiation into electrical energy (such as a photovoltaic device or solar cell, radiation detectors);

d. devices that respond to electrical or magnetic energy such as a liquid crystal display, radio-frequency ID tags;

e. devices that respond to a change in chemical environment such as chemical specific and non-specific sensors, gas sensors, and f. devices that include one or more electronic components that include one or more organic semiconductor layers (e.g., a transistor, diode or other semiconductor), metal-semiconductor junctions (e.g., Schottky barrier diodes), p-n junction diodes, p-n-p-n switching devices, bipolar junction transistors (BJTs), heterojunction bipolar translators, switching transistors, charge transfer devices, thin film transistors, tunable microcavities for variable output wavelength, telecommunications devices and applications, optical computing devices, optical memory devices and field effect transistors, as well as combinations thereof.

The term, "device," also includes coating materials for memory storage devices, such as, electronic memory for electronics (particularly computer memory), antistatic films, biosensors, electrochromic devices, solid electrolyte capacitors, energy storage devices such as, a rechargeable battery, and electromagnetic shielding applications.

All such devices may be assembled into circuits, display devices, radio frequency tags and the like. Such a device can have the composition of interest in a thin film, but may be used in a block. The compositions also can be used in a device to modify the surfaces of other material components with the aim of improving mechanical contact between materials and/or improving charge transport from one material to another and/or to provide a good metal/organic charge transfer interface. Other protective coatings, binders and charge conductors may be added. The thickness of each layer can depend on the application and the composition, and the other layers in the device.

A further embodiment of the present invention is the formation of a pattern of components in a device, such as, a pattern formed by aligned self-assembled monolayers (SAMs).

The fluoroacyl arylamines of the present invention may also be used in applications not traditionally considered for organic electronic devices, such as, for photocatalysts and electro catalysts to catalyze synthesis and degradation chemical reactions.

For many electronic and chemical applications, an energy band gap is desired and may be estimated by optical adsorption spectra, such as, in the UV-vis range. Electron and hole transport mobilities may be estimated by comparison to other organic compounds based on, for example, adsorption.

To utilize the more abundant wavelengths of light, materials with lower energy band gaps can be used. That allows use of the more common visible light instead of UV. The fluoroacyl arylamine derivatives have altered HOMO-LUMO energy levels from the non-derivatized parent arylamine and therefore have correspondingly different applications. Due to the similar transport mobilities with current photoreceptor hole transport materials, the compositions of interest can be used as charge transport materials, for example, in electrophotographic imaging. Also, because the electron and hole affinities are acceptable, the materials of the present invention are expected to acceptably transport both holes and electrons for a wide variety of electronic applications.

Furthermore, fluoroacyl groups cause red-shifting of the adsorption bands relative to the non-fluoroacyl parent compound. That permits use of longer wavelengths of light allowing, for example, use of a blue laser instead of UV and also single layer photoreceptor designs.

Organic light emitting diodes ("OLED"), for example, for displays, where the organic active layer is sandwiched between two electrical contact layers can comprise a fluoroacyl arylamine of interest. In an OLED, the organic photoactive layer emits light through the light-transmitting electrical contact layer on application of a voltage across the electrical contact layers.

Since the compositions of the present invention may be used as either p-type semiconductor carriers, (those that carry holes) or n-type semiconductor carriers (those that carry electrons), either layer may use the compositions of interest. A single layer OLED also may be made using a composition of interest. Polymerized and cross-linked versions of the fluoroacyl arylamines, for example, dispersed in a mixture, can be suitable for such use, for example, in a p-type semiconductor.

Multiple layers of semiconductors may be used with suitable insulating layers therebetween. The insulating layer may be a diverse material or a highly doped region of one of the layers. Also provided are pattern multilayers of semiconductors where the pattern is provided by locally doped regions in the circuit.

One or more semiconductor dyes or electroluminescent compounds also may be added to an OLED.

An OLED can comprise at least an anode (electron blocking layer or hole injection electrode), a cathode (hole blocking layer or electron injection electrode) and an electroluminescent layer. An OLED optionally comprises other layers, such as, a hole injection layer (s), a hole transport layer (s), an electron injection layer (s), an electron transport layer (s), a dopant, an insulator (s), a conductor or interconnect.

The electron blocking layer (hole injection electrode) can be made of an inert metal or an alloy. A more transparent electron blocking layer (hole injection electrode) material, such as, an indium-doped tin oxide (ITO) can be used. Conductive polymers also can be used in transparent hole-injection electrodes. The electron blocking layer (hole injection electrode) can be from about 50 to about 300 nm in thickness.

The electron injection electrode can be made of a metal or an alloy, or a laminant having aluminum, calcium or magnesium, though other materials may be used. A variety of inorganic compounds, particular rare earth metals and organic compounds may be used as dopants.

Insulators may be inorganic, organic or a composite thereof. When the insulator is patterned, the insulator may perform the function of a blocking layer between OLED materials.

A photoactive material may be used alone, or in or with a polymer or the like, such as, in a CTL. The light-emitting layer can also be an electron transport layer. Generally, a polymer used is one through which light may be transmitted therethrough with little interference. Compounds, such as, fluorescent dyes, small molecule organic fluorescent compounds, fluorescent and phosphorescent metal complexes, conjugated polymers, and mixtures thereof may be added to enhance the color and contrast of the light being emitted.

In a light-emitting electrochemical cell (LEC), the charged semiconductor molecules are mobile and are oxidized at the anode and reduced at the cathode. In an LEC, the anode (such as, ITO) and the cathode (such as, aluminum) can be separated by an organic layer where reduced molecules with anions provide holes and the oxidized molecules with cations yield electrons, which meet to produce light. The fluoroacyl arylamines may be used for either or both charge transport functions.

Photovoltaic materials, which include mixtures and conjugated polymers and nano-particles or nano-crystals of inorganic material, may be used with the compositions of interest.

In organic photovoltaics, light passes by or through the anode (for example, ITO) and strikes the layer containing organic electron donor (p-semiconductor). Electrons pass to an adjacent organic electron acceptor (n-semiconductor) and onto the cathode (such as, aluminum). The fluoroacyl arylamines may be used in either or both layers.

Alternative to discrete layers, both organics can be dispersed in a heterojunction layer where the two semiconductors are blended in different phases. The morphology of the heterojunction is configured so that the electrons and holes can migrate to the respective electrodes and not be trapped in an isolated island. However, the fluoroacyl arylamines have both charge transport functions and thus, electrons and holes are less likely to be trapped and the morphology of the device is less critical.

Furthermore, the bulk of energy from sunlight and most artificial light is not UV but rather visible and longer wavelengths. The compounds of interest have a red-shifted adsorption maximum and therefore utilize more energy from ambient or artificial light. To recover more energy from light, photovoltaic devices comprising a fluoroacyl arylamine may be used in combination with conventional photovoltaics, either inorganic or with other organics. Separate layers may be employed to adsorb different wavelengths of light. An additional oxidized/reduced dye molecule may be added which may further narrow the band gap.

An example of the benefits of a photovoltaic usable at longer wavelengths include detection of a blue laser instead of UV. UV light is adsorbed by a number of common materials whereas a blue laser is not. Greater sensitivity in the visible region provides for a more sensitive photoreceptor for light.

Photovoltaic activity may be applied to a number of uses such as in sensors that respond to radiant energy to generate a signal. The device may generate a signal with or without an applied bias voltage, such as, is used in a photodetector.

To further enhance the sensitivity of the photodetector, non-reflective, antiglare and light trapping coatings may be used. A light-trapping coating can be variable in thickness and can comprise structures, such as, small domes or bubbles, or may comprise and embossed polymer, which capture and optionally refract light from indirect angles.

Other organic electronic devices are known to be optically or electrically responsive. The fluoroacyl arylamines may be used therein in a manner similar to other organic charge transport compositions.

The disclosure is not limited to particular embodiments described herein, and some components and processes may be varied by one of skill, based on the disclosure. The terminology used herein is for the purpose of describing particular embodiments only and is not intended to be limiting.

Various aspects of the embodiments of interest now will be exemplified in the following non-limiting examples.

EXAMPLES

Example 1

Synthesis of DFA-Tetraphenylenebiphenyldiamine

To a 100 ml flask containing 30 ml DCM (dichloromethane) were added 2.44 g (5.0 mmol, 1.0 equivalent) of tetraphenylenebiphenyldiamine (TBD) to yield a beige slurry. Then, 5.6 ml (40 mmol, 8.0 equivalents) of TFAA (trifluoroacetic anhydride) were poured into the mixture and the flask equipped with a reflux condenser. The mixture was heated to reflux (40° C.), the reactant dissolving to form a dark brown solution. The reaction was stirred for 72 hours at the reflux temperature.

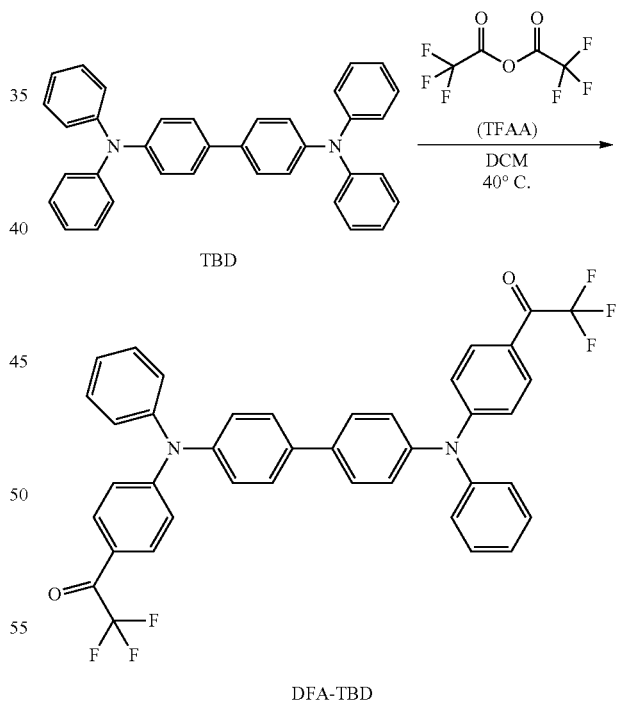

When the reaction was complete (determined by HPLC to be >99% conversion), the mixture was cooled to room temperature then diluted with 30 ml DCM. The solution was then poured into 25 ml of stirring $H_2O$. The organic layer was isolated and washed with two 10 ml portions of a 1/1 mixture of $H_2O$/saturated $NaHCO_3$ and one 10 ml portion of a sodium chloride buffer, such as, a saturated NaCl solution. The aqueous wash which contains the acid byproduct was removed.

That solution has a pH approaching neutral. The DCM solution then was dried with $Na_2SO_4$ and removed by evaporation to yield di(trifluoroacyl) (DFA)-tetraphenylenebiphenyldiamine (TBD) as 1.2 g (70%) of a golden yellow solid. The chemical structure was confirmed by nuclear magnetic resonance with $^1H$ NMR (300 MHz, $CH_2Cl_2$-d2) δ 7.93 (d, J=8.4 Hz, 4H), 7.60 (d, J=8.4 Hz, 4H), 7.42 (dd, J=7.3 Hz, 2H), 7.27-7.24 (12H), 7.04 (d, J=9.0 Hz, 4H); and $^{19}F$ NMR (300 MHz, $CH_2Cl_2$-d2) δ 71.2 (s, 6F).

Example 2

Synthesis of DFA-Para-methyl tetraphenylenebiphenyldiamine

To a 100 ml flask containing 30 ml DCM were added 2.58 g (5.0 mmol, 1.0 equivalent) of para-methyl tetraphenylenebiphenyldiamine (pTBD) to yield a beige slurry. Then, 2.8 ml (20 mmol, 8.0 equivalents) of TFAA were poured into the mixture and the flask equipped with a reflux condenser. The mixture was heated to reflux (40° C.), the reagent dissolving to form a dark red-brown solution. The reaction was stirred for 48 hours at the reflux temperature.

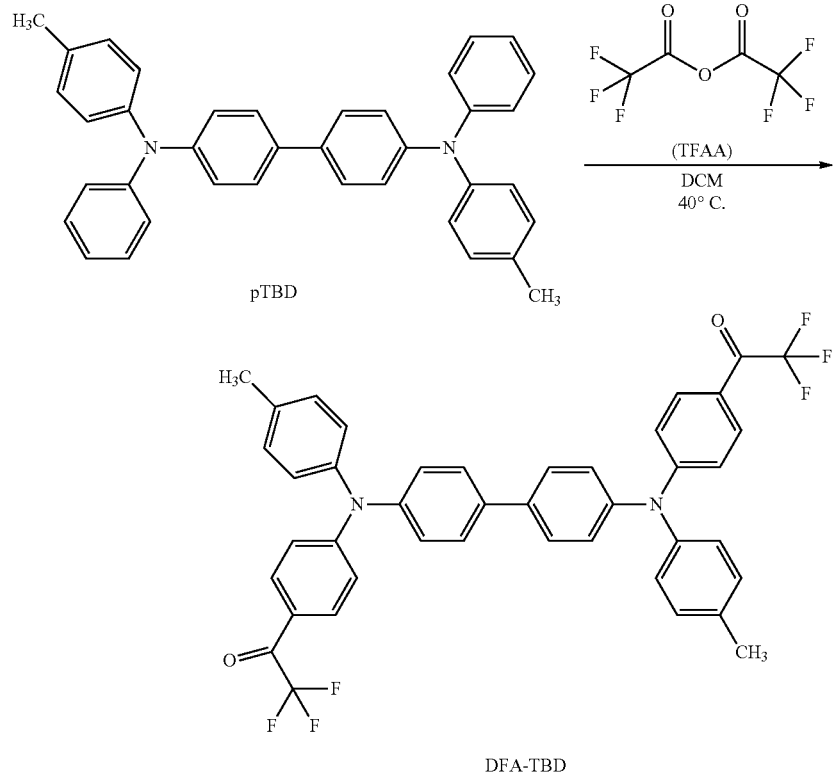

When the reaction was complete (determined by HPLC to be >99% conversion), the mixture was cooled to room temperature then diluted with 30 ml DCM. The solution was then poured into 25 ml of stirring $H_2O$. The organic layer was isolated and washed with two 10 ml portions of a 1/1 mixture of $H_2O$/saturated $NaHCO_3$ and one 10 ml portion of NaCl buffer. The neutral pH aqueous wash which contains the acid byproduct was removed. The DCM solution then was removed by evaporation to yield the DFA product as 3 g (85%) of amber solid. The chemical structure was confirmed by nuclear magnetic resonance with $^1H$ NMR (300 MHz, $CH_2Cl_2$-d2) δ7.91 (d, J=8.4 Hz, 4H), 7.58 (d, J=8.4 Hz, 4H), 7.27-7.10 (12H), 7.01 (d, J=9.3 Hz, 4H), 2.40 (s, 6H); and $^{19}F$ NMR (300 MHz, $CH_2Cl_2$-d2) δ71.1 (s, 6F).

Example 3

Electronic Absorption Properties of TBD and pTBD and Fluoroacylated Derivatives Thereof The electronic absorption spectra in the UV and visible range of TBD and DFA-TBD were obtained and compared.

An approximate 40 nm red shift of absorption band in DFA-TBD relative to that of TBD was observed.

Similarly, the electronic absorption spectra in the UV and visible range of pTBD and DFA-pTBD demonstrated an approximate 40 nm red shift of absorption band for DFA-pTBD relative to that of pTBD.

Hence, the fluoroacyl groups alter HOMO-LUMO energy levels.

Example 4

Fabrication of a Charge Transport Device

Free standing films of DFA-TBD and DFA-pTBD were made with a 1:1 ratio of charge transport molecule and polycarbonate (PCZ-800). Solutions in DCM were cast as films onto metalized Mylar substrates. The film was dried in an actively vented oven at 120° C. for 40 minutes. The dried film was delaminated by pealing and used for further testing.

Example 5

Charge Transport Properties

Time of flight measurements for both electrons and holes were made for DFA-TBD in polycarbonate and DFA-pTBD in polycarbonate as described above.

The field used during measurement was at $2.8\,E^{-5}$ (V/cm).

The observed data demonstrate the charge transporting property of the fluoroacylated arylamines, which transport both holes and electrons with mobilities ranging from $10^{-6}$ to $10^{-5}\,V^{-1}\,s^{-1}$, comparable to known charge transport materials.

Example 6

Fabrication of a Photoreceptor Device and Testing

Polycarbonate (PCZ-800, Mitsubishi) and separately, either DFA-TBD or DFA-pTBD, were mixed in a 1:1 ratio and dissolved in DCM. Films were cast from the mixture onto Tigris (AMAT) substrates. The films were dried in an actively vented oven at 120° C. for 40 minutes. The films resulted in defect-free charged transport layers which were incorporated into photoreceptors.

The photoreceptors, along with a control comprising a commercially available charge transfer molecule, were tested in a UDS scanner set to obtain photoinduced discharge cycles, sequenced at one charge-erase cycle followed by one charge-expose-erase cycle, wherein the light intensity was incrementally increased with cycling to produce a series of photoinduced discharge characteristic curves (PIDC) from which the photosensitivity and surface potentials at various exposure intensities were measured. The scanner was equipped with a scorotron set to a constant voltage charging at various surface potentials. The photoconductors were tested at surface potentials of 700 volts with the exposure light intensity incrementally increased by regulating a series of neutral density filters; the exposure light source was a 780 nm xenon lamp. The xerographic simulation was conducted in an environmentally controlled light tight chamber at dry conditions (10% relative humidity and 22° C.). The devices were tested for $V_{high}$ and $V_{low}$ with a 780 nm exposure and erase, and 117 ms timing.

The PIDC data for the above devices demonstrated suitable charging by the fluoroacylated arylamines of interest, comparable to that of the known charge transfer molecule.

It will be appreciated that various of the above-discussed and other features and functions, (or alternatives thereof) desirably may be combined into other different systems or applications. Also, that various presently unforeseen or unanticipated alternatives, modifications, variations or improvements therein may be subsequently made by those skilled in the art also are intended to be encompassed by the following claims.

All references cited herein are herein incorporated by reference in entirety.

We claim:

1. A fluoroacyl arylamine comprising an arylamine portion and one or more fluoroacyl groups, comprising:

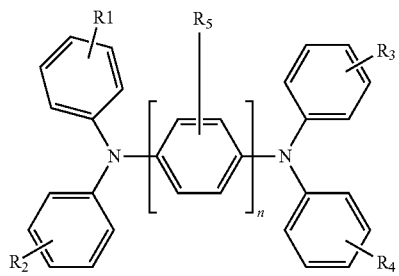

wherein each of $R_1$, $R_2$, $R_3$, $R_4$ and $R_5$ is located at any site on an aryl group; and is one or more hydrogen atoms; a halogen, a hydrocarbon of 1 to about 8 carbon atoms, which can be substituted or can comprise a heteroatom, or a functional group; n is 1, 2 or 3; and at least one ring comprises at least one fluoroacyl group.

2. The fluoroacyl arylamine of claim 1 comprising:

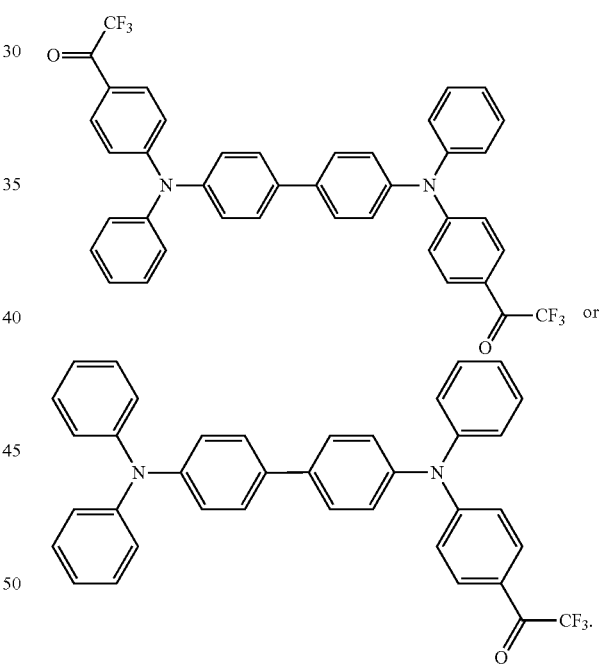

3. The fluoroacyl arylamine of claim 1 comprising:

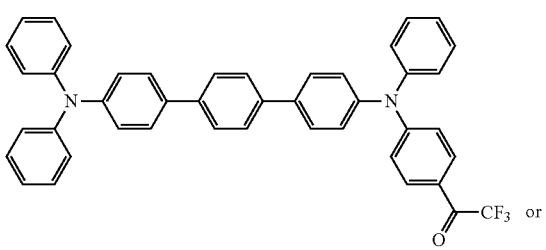

-continued

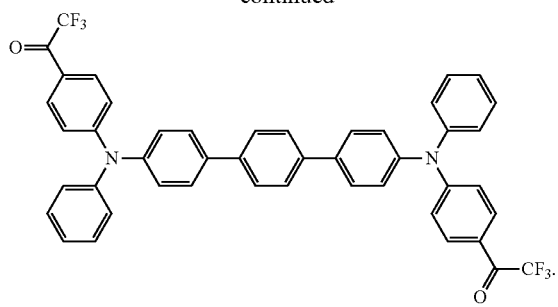

4. The fluoroacyl arylamine of claim 1 comprising:

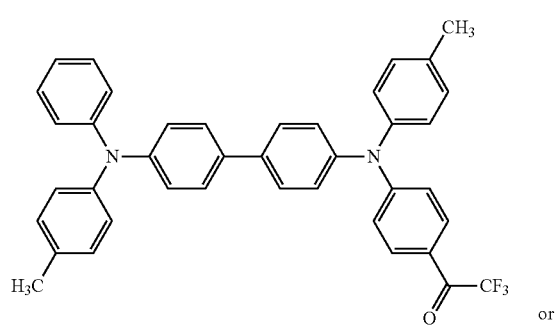

or

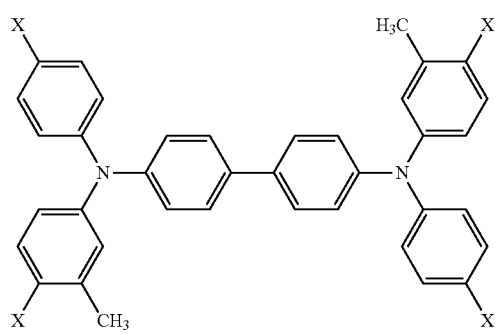

5. The fluoroacyl arylamine of claim 1 comprising:

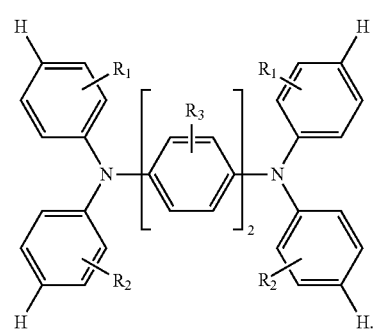

wherein X is a fluoroacyl group or hydrogen and the number of fluoroacyl groups ranges from 1 to 4.

6. A fluoroacyl arylamine comprising structure A or B comprising an arylamine portion and one or more fluoroacyl groups:

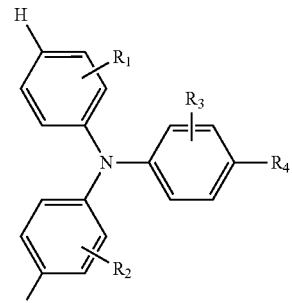

A wherein $R_1$, $R_2$ and $R_3$ each is hydrogen, $C_1$-$C_5$ alkyl, $C_3$-$C_7$ cyclic alkyl, $C_1$-$C_4$ alkoxy, hydroxyl, ω-hydroxy substituted $C_2$-$C_8$ alkyl, halogen, or aryl, optionally substituted with $C_1$-$C_5$ alkyl $R_4$ is hydrogen, $C_1$-$C_5$ alkyl, $C_3$-$C_7$ cyclic alkyl, hydroxyl, ω-hydroxy substituted $C_2$-$C_8$ alkyl, halogen or aryl, optionally substituted with $C_1$-$C_5$ alkyl; and at least one ring comprising at least one fluoroacyl moiety
or

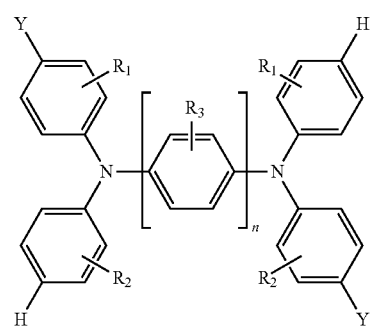

B wherein Y is hydrogen, $C_1$-$C_5$ alkyl, $C_3$-$C_7$ cyclic alkyl, $C_1$-$C_4$ alkoxy, hydroxyl, ω-hydroxy substituted $C_2$-$C_8$ alkyl, halogen or aryl, optionally substituted with $C_1$-$C_5$ alkyl, $R_1$, $R_2$ and $R_3$ each is hydrogen, $C_1$-$C_5$ alkyl, $C_3$-$C_7$ cyclic alkyl, $C_1$-$C_4$ alkoxy, hydroxy, ω-substituted $C_2$-$C_8$ alkyl, halogen or aryl, optionally substituted with $C_1$-$C_5$ alkyl; n is 1, 2 or 3; and at least one ring comprises at least one fluoroacyl moiety.

7. The fluoroacyl arylamine of claim 6, comprising structure A, wherein $R_4$ is hydrogen.

8. The fluoroacyl arylamine of claim 6, wherein structure B comprises:

9. The fluoroacyl arylamine of claim 6, wherein said arylamine portion comprises:

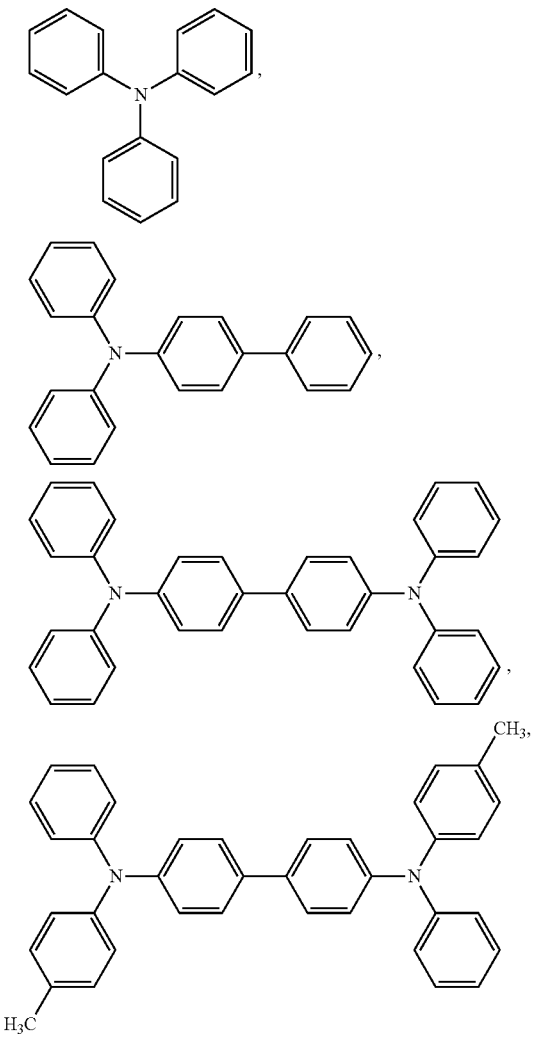

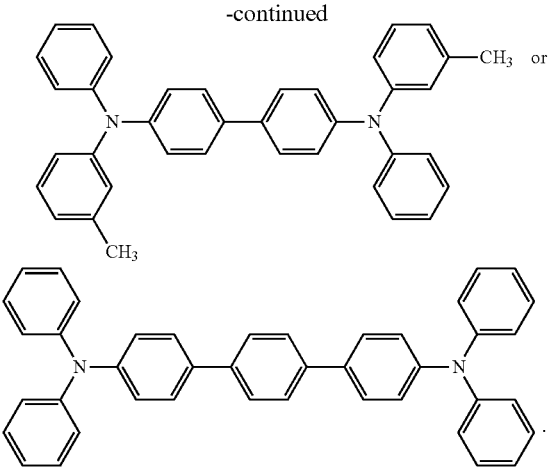

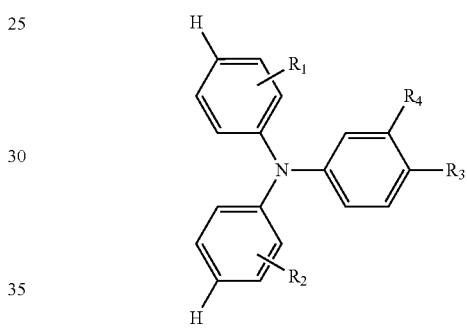

10. The fluoroacyl arylamine of claim 6, comprising structure B, wherein Y is methyl.

11. A fluoroacyl arylamine comprising the structure:

wherein $R_1$, $R_2$ and $R_3$ each is hydrogen, $C_1$-$C_5$ alkyl, $C_3$-$C_7$ cyclic alkyl, $C_1$-$C_4$ alkoxy, hydroxyl, ω-hydroxy substituted $C_2$-$C_8$ alkyl, halogen or aryl, optionally substituted with $C_1$-$C_5$ alkyl; $R_4$ is hydrogen, $C_1$-$C_5$ alkyl, $C_3$-$C_7$ cyclic alkyl, hydroxyl, ω-hydroxy substituted $C_2$-$C_8$ alkyl, halogen or aryl, optionally substituted with $C_1$-$C_5$ alkyl; and at least one ring comprising at least one fluoroacyl moiety.

* * * * *